United States Patent
Garnavi et al.

(10) Patent No.: US 9,949,643 B2
(45) Date of Patent: Apr. 24, 2018

(54) AUTOMATIC VISUALIZATION OF REGIONAL FUNCTIONAL PARAMETERS OF LEFT VENTRICLE FROM CARDIAC IMAGING

(71) Applicant: International Business Machines Corporation, Armonk, NY (US)

(72) Inventors: Rahil Garnavi, Calrton (AU); Xi Liang, Calrton (AU); Tanveer Fathima Syeda-Mahmood, Cupertino, CA (US); Simon Frank Wail, Ormond (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 137 days.

(21) Appl. No.: 14/536,616

(22) Filed: Nov. 8, 2014

(65) Prior Publication Data
US 2016/0110879 A1    Apr. 21, 2016

Related U.S. Application Data

(60) Provisional application No. 62/065,636, filed on Oct. 18, 2014.

(51) Int. Cl.
*G06T 7/00* (2017.01)
*A61B 5/00* (2006.01)
(Continued)

(52) U.S. Cl.
CPC ............ *A61B 5/0044* (2013.01); *A61B 5/055* (2013.01); *G06T 7/0012* (2013.01);
(Continued)

(58) Field of Classification Search
CPC ....... A61B 5/0044; A61B 5/055; G06T 7/136; G06T 7/0016; G06T 7/0012; G06T 7/20;
(Continued)

(56) References Cited

U.S. PATENT DOCUMENTS 5,800,355 A * 9/1998 Hasegawa .............. A61B 6/583
                                                          382/128
6,248,070 B1 * 6/2001 Kanda ...................... A61B 8/06
                                                          128/916
(Continued)

FOREIGN PATENT DOCUMENTS

CN        102397070        4/2012

OTHER PUBLICATIONS

Cerqueira, Manuel D., et al. "Standardized myocardial segmentation and nomenclature for tomographic imaging of the heart a statement for healthcare professionals from the cardiac imaging committee of the Council on Clinical Cardiology of the American Heart Association." Circulation 105.4 (2002): 539-542.*

(Continued)

*Primary Examiner* — Siamak Harandi
*Assistant Examiner* — Carol Wang
(74) *Attorney, Agent, or Firm* — Louis J. Percello; Otterstedt, Ellenbogen & Kammer, LLP

(57) ABSTRACT

A method for automatically identifying and localizing anatomical regions of a left ventricle of a heart using a segment model, the method including receiving a volumetric MR image series of one or more time-points in a heart cycle with associated myocardial boundaries, representing the heart, performing a long-axis partitioning on each image of the volumetric image series, performing a short-axis partitioning volumetric image series, generating a polar map, wherein each image of the volumetric image series is mapped to a location on the polar map, wherein the location is characterized using the long-axis partitioning and the short-axis partitioning, and generating a mapping from the polar map to a voxel in an associated image of the volumetric image series representing an anatomical location.

9 Claims, 5 Drawing Sheets

(51) Int. Cl.
  *G06T 7/20* (2017.01)
  *G06T 11/00* (2006.01)
  *A61B 5/055* (2006.01)
  *G06T 7/136* (2017.01)

(52) U.S. Cl.
  CPC ............ G06T 7/0016 (2013.01); G06T 7/136 (2017.01); G06T 7/20 (2013.01); G06T 11/008 (2013.01); *G06T 2207/10076* (2013.01); *G06T 2207/10081* (2013.01); *G06T 2207/10088* (2013.01); *G06T 2207/10104* (2013.01); *G06T 2207/30048* (2013.01)

(58) Field of Classification Search
  CPC ......... G06T 11/008; G06T 2207/10076; G06T 2207/10104; G06T 2207/10081; G06T 2207/30048; G06T 2207/10088
  See application file for complete search history.

(56) References Cited

U.S. PATENT DOCUMENTS

| | | | |
|---|---|---|---|
| 6,275,613 B1* | 8/2001 | Aiger | G06K 9/6203 382/195 |
| 7,561,909 B1 | 7/2009 | Pai | |
| 7,907,759 B2 | 3/2011 | Hundley | |
| 8,107,703 B2 | 1/2012 | Shekhar | |
| 8,483,462 B2 | 7/2013 | Kiraly | |
| 8,538,103 B2 | 9/2013 | Chono | |
| 8,542,894 B2 | 9/2013 | Bernhardt | |
| 8,583,209 B2 | 11/2013 | Maier | |
| 8,649,584 B2 | 2/2014 | Kawasaki | |
| 8,755,575 B2 | 6/2014 | Hautvast | |
| 2003/0176780 A1* | 9/2003 | Arnold | G06T 7/0012 600/407 |
| 2004/0087853 A1* | 5/2004 | Fujisawa | A61B 6/032 600/425 |
| 2005/0240094 A1 | 10/2005 | Pichon | |
| 2006/0045328 A1* | 3/2006 | Jacob | G06T 17/00 382/154 |
| 2006/0182341 A1* | 8/2006 | Rinck | G06K 9/3233 382/173 |
| 2007/0014452 A1* | 1/2007 | Suresh | G06F 19/3437 382/128 |
| 2008/0008366 A1* | 1/2008 | Desh | G06T 19/00 382/128 |
| 2008/0044072 A1 | 2/2008 | Kiraly | |
| 2008/0199064 A1* | 8/2008 | Gerard | A61B 8/08 382/131 |
| 2009/0161938 A1* | 6/2009 | Shekhar | A61B 8/0883 382/131 |
| 2009/0208078 A1* | 8/2009 | Fritz | G06T 7/0012 382/130 |
| 2010/0041992 A1* | 2/2010 | Ohuchi | A61B 8/08 600/443 |
| 2010/0074487 A1* | 3/2010 | Miyamoto | A61B 6/503 382/128 |
| 2010/0215238 A1 | 8/2010 | Lu | |
| 2010/0266176 A1* | 10/2010 | Masumoto | G06F 19/321 382/128 |
| 2011/0007953 A1* | 1/2011 | Bernhardt | G06T 11/206 382/128 |
| 2011/0249005 A1* | 10/2011 | Hautvast | A61B 5/055 345/440 |
| 2012/0089016 A1* | 4/2012 | Mizuno | G06T 11/206 600/425 |
| 2012/0245460 A1* | 9/2012 | Slomka | A61B 5/02755 600/425 |
| 2012/0310074 A1* | 12/2012 | Yamamori | A61B 6/503 600/407 |
| 2013/0060156 A1* | 3/2013 | Gregg | A61B 5/04011 600/523 |
| 2014/0081125 A1* | 3/2014 | Zhou | A61B 5/0044 600/419 |
| 2015/0206302 A1* | 7/2015 | Chen | G06T 7/0012 382/131 |

OTHER PUBLICATIONS

Silva, Samuel, Beatriz Sousa Santos, and Joaquim Madeira. "Exploring different parameters to assess left ventricle global and regional functional analysis from coronary ct angiography." In Computer Graphics Forum, vol. 31, No. 1, pp. 146-159. Blackwell Publishing Ltd, 2012.*

Dominik Fritza, et al., "Automatic Segmentation of the Left Ventricle and Computation of Diagnostic Parameters using Regiongrowing and a Statistical Model," Institute for Computer Design and Fault Tolerance, University of Karlsruhe Haid-und-Neu-Straβe 7, 76131 Karlsruhe, Germany, Proc. SPIE, pp. 1-11, Apr. 29, 2005; DOI: 10.1117/12.595071.

H. Lombaert, et al., "Spatio-Temporal Segmentation of the Heart in 4D MRI Images Using Graph Cuts With Motion Cues," E'colePolytechniquedeMontre'al,Montreal,Canada, Nano to Macro, 2010 IEEE International Symposium on Biomedical Imaging, pp. 492-495, Apr. 14-17, 2010; DOI: 10.1109/ISBI.2010.5490303.

Rahilv Garnavi et al., unpublished U.S. Appl. No. 14/986,541, filed Dec. 31, 2015, Automatic Isualization of Regional Functional Parameters of Left Ventricle From Cardiac Imaging, pp. 1-22 and 5 sheets of drawings.

List of IBM Patents or Patent Applications.

* cited by examiner

AUTOMATIC VISUALIZATION OF REGIONAL FUNCTIONAL PARAMETERS OF LEFT VENTRICLE FROM CARDIAC IMAGING

CROSS-REFERENCE TO RELATED APPLICATIONS

This application claims the benefit of U.S. Provisional Patent Application No. 62/065,636 filed on Oct. 18, 2014, the complete disclosure of which is herein expressly incorporated by reference in its entirety for all purposes.

BACKGROUND

The present disclosure relates to methods for imaging, and more particularly to a method for generating a polar map to visualize regional functional parameters extracted from cardiac imaging data.

Assessment of left ventricular abnormalities in magnetic resonance images is widely accepted as a predictor of cardiac disease. The quantitative assessment of the left ventricle (LV) includes global and regional measurements.

In most computer-aided diagnosis systems of cardiac magnetic resonance imaging (MRI), the global functional parameters are commonly available, such as ejection fraction, LV mass, stroke volume, end-diastolic volume and end-systolic volume.

The LV regional assessment typically relies on the visual inspection, analysis and interpretation of cine images of the left ventricle in multiple planes and the interpretation of LV regional functions. Studies have shown that this method may be inaccurate, time consuming and suffer from high inter-observer variability.

BRIEF SUMMARY

According to an exemplary embodiment of the present invention, a method for automatically identifying and localizing anatomical regions of a left ventricle of a heart using a segment model, the method including receiving a volumetric image series of one or more time-points in a heart cycle with associated myocardial boundaries, representing the heart, performing a long-axis partitioning on each image of the volumetric image series, performing a short-axis partitioning on each image of the volumetric image series, generating a polar map, wherein each image of the volumetric image series is mapped to a location on the polar map, wherein the location is characterized using the long-axis partitioning and the short-axis partitioning, and generating a mapping from the polar map to a voxel in an associated image of the volumetric image series representing an anatomical location.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Figure 1:
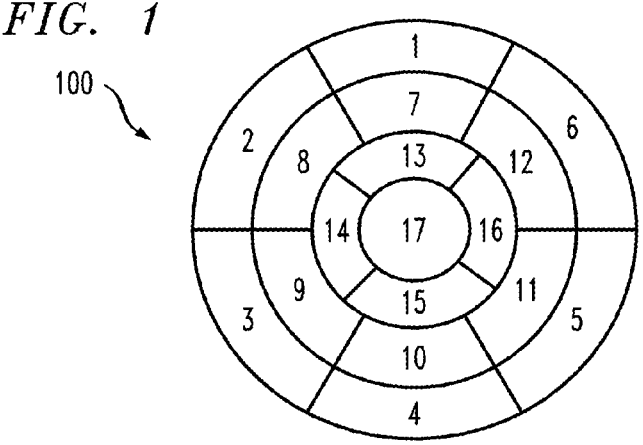
FIG. 1 is a polar map according to an exemplary embodiment of the present invention.

According to an exemplary embodiment of the present invention, functional parameters of a heart are visualized in cardiac MRI using a 2-dimensional (2D) polar map (see FIG. 1). Cardiac magnetic resonance (MR) images are 3D+cine images, which enable the assessment of a beating heart. According to an exemplary embodiment of the present invention, a 1-to-1 linkage is built from volumetric cardiac MR images series of one or more time-points in the heart cycle to a 2D color-coded polar map. Various functional parameters can be represented in the polar map, such as the LV wall motion and thickness.

Figure 2:
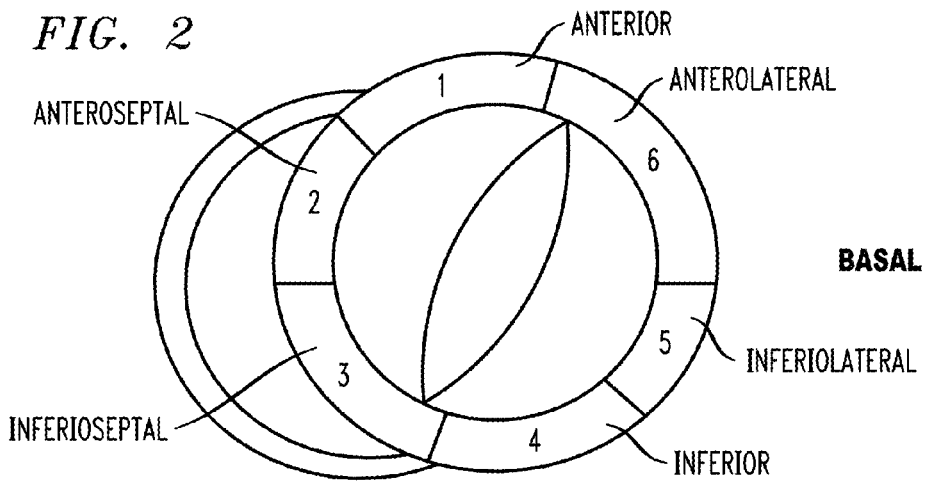
FIG. 2 shows a basal segmentation according to an exemplary embodiment of the present invention.
Figure 3:
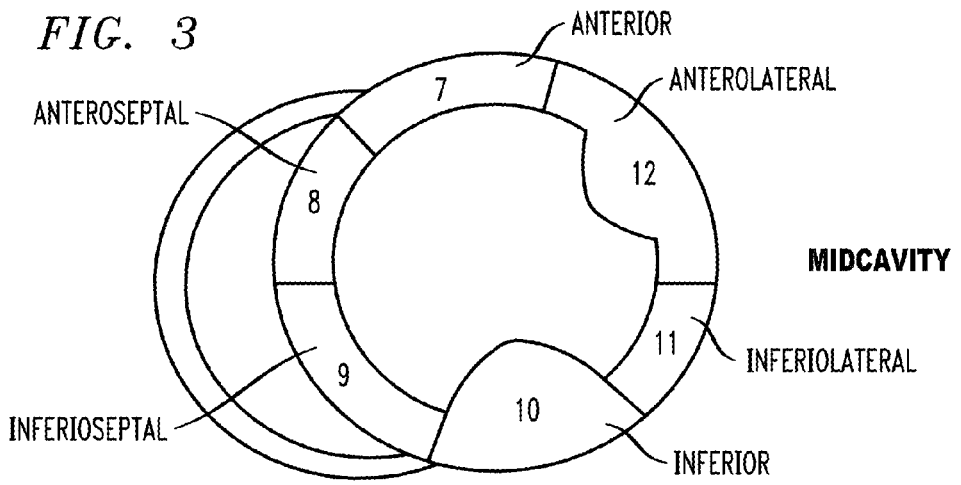
FIG. 3 shows a mid-cavity segmentation according to an exemplary embodiment of the present invention.
Figure 4:
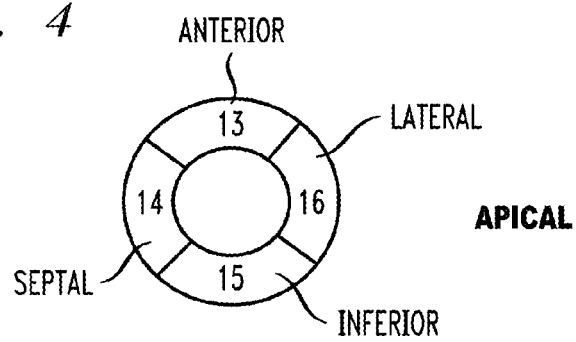
FIG. 4 shows an apical segmentation according to an exemplary embodiment of the present invention.
Figure 5:
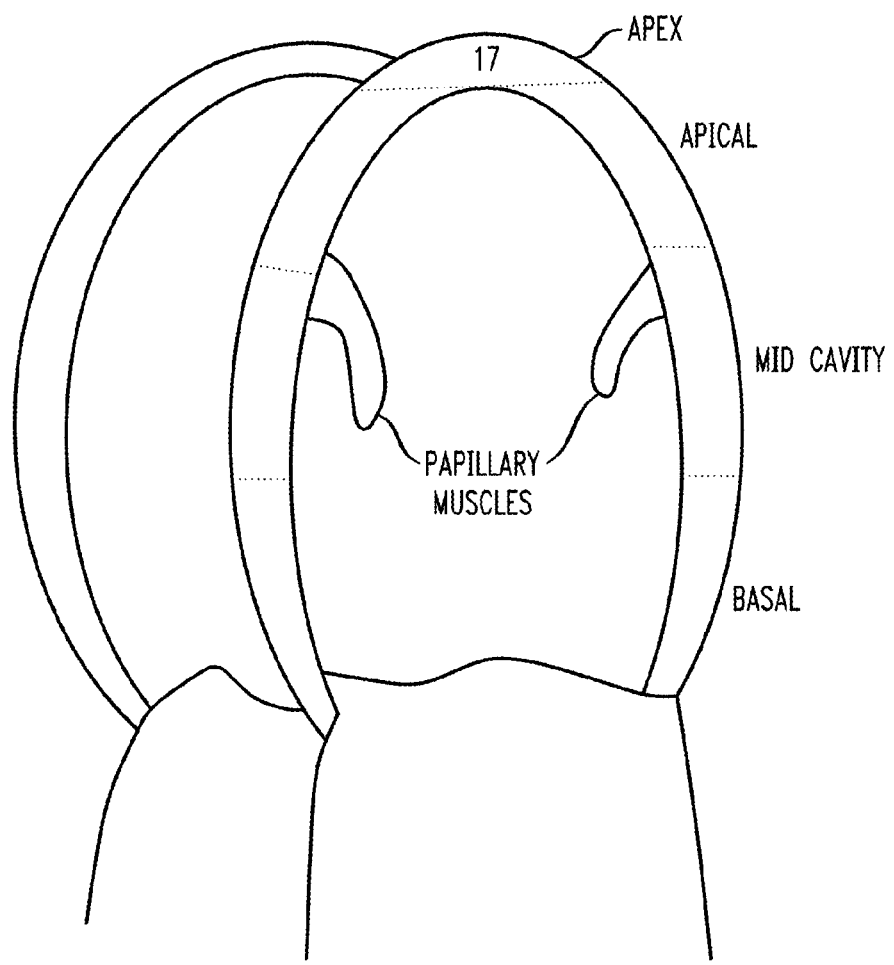
FIG. 5 shows region layers in a long axis plane according to an exemplary embodiment of the present invention.

The LV regional assessment typically relies on the visual inspection, analysis and interpretation of cine images of the left ventricle in multiple planes and the interpretation of LV regional functions. For example, LV wall (myocardium) motion is an important regional assessment in evaluating the LV. The diagnosis of abnormal LV wall motion is generally based on the reading of cardiac magnetic resonance (MR) cine images. In clinical practice, heart wall motion is scored by following a standard issued by American Heart Association (AHA), where 17 myocardial segments are graded from cine-MR images in the short-axis plane-cardiac slices from the base (top) (FIG. 2) to the apex (bottom) (FIG. 4). A mapping of a 17 segment model to a polar map is shown in FIG. 2 through FIG. 4. FIG. 5 shows region layers of FIG. 2 through FIG. 4 in the long-axis plane.

According to an exemplary embodiment of the present invention, an automated segment extraction and visualization system generates a polar map to visually evaluate measurements within specific anatomical regions. Extracted segments can be used in further automated analysis and diagnosis, such as hypertrophy (LV wall thickening) detection or infarct transmurality (level of LV tissue damage due to a heart attack). Extracted segments can be automatically correlated across different imaging modalities as well as different image series over time.

According to an exemplary embodiment of the present invention, the automated segment extraction and visualization system includes a framework that automatically identifies and localizes a plurality of anatomical regions of the left ventricle. Any functional measurements, such as motion, thickness, etc., performed on these regions can be used to automatically generate a polar map in which the measurements can be represented by color range, shading, different patterns, etc. In the polar map, anatomical location is directly related to the specific segment in the model. The polar map is used to visualize the regional functional parameters. The polar map has a 1-to-1 linkage to the corresponding location within the heart. The polar map automatically directs a user to tissue or its functional parameters from a corresponding location on the polar map.

Figure 6:
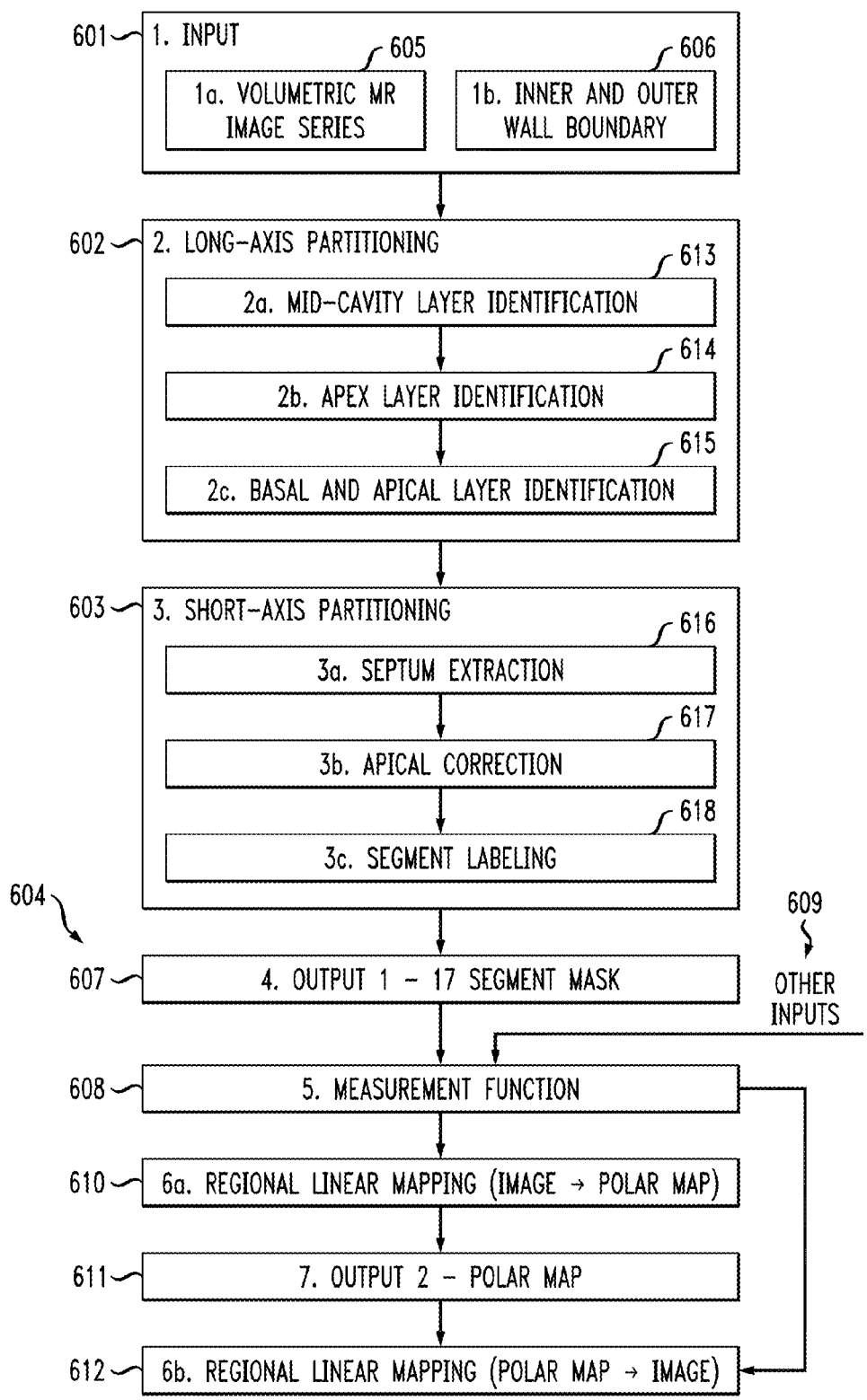
FIG. 6 is a flowchart of a method according to an exemplary embodiment of the present invention.

In one or more embodiments of the present invention, a method for automatically generating a polar map of the LV in a segment model (see FIG. 6) includes long-axis partitioning 602, short-axis partitioning 603, and polar map generation 604. The method is applied on all 2D MR slices of a certain time phase in a cine cardiac MRI series, such as end-diastole. The method takes input 601 including a volumetric MR image series 605 with the associated myocardial boundaries 606. The method outputs a segment mask 607 for all tissue in the LV, a polar map 611 to represent the regional functional parameters extracted from the LV 610, and a mapping from the polar map to the anatomical location in the cardiac MRI series 612. FIG. 6 is the flowchart of an exemplary framework.

At block 601, the input includes a volumetric MR image series 605. The volumetric MR image series includes 2D MR slices in the short-axis plane. The slices are from the same cardiac phase. The input 601 further includes the corresponding inner and outer LV wall boundaries 606.

At block 602, long-axis partitioning includes labeling each slice according to its location from the base (top) to the apex (bottom) of the heart. These locations can include basal, mid-cavity, apical and apex.

At block 613, mid-cavity layer identification is performed. The mid-cavity is selected from the region that includes the entire length of the papillary muscles (PMs) at end-diastole (ED). The PMs are used as anatomic landmarks to select mid-cavity slices. This involves identifying candidate regions of PMs by subtracting endocardium (inner LV wall) from blood pool masks, using, for example a Ostu thresholding or other image thresholding method. The candidate regions are examined for size. If the regions are determined to be larger than a threshold, e.g., via morphological processing, than they are considered as PMs. Any slices that were found to have PMs are selected as belonging to the mid-cavity.

At block 614, apex layer identification is performed. A feature of the apex is an area of the myocardium beyond the end of the left ventricular cavity where this is no blood pool. On a typical MR slice, blood pools appear as a relatively bright area and myocardium and surrounding structures appear as a relatively dark area. Based on these features, the apex can be localized by detecting if a blood pool exists. The blood pool is the area inside the inner LV wall boundary, which is available from the input 601. If the slice does not have inner wall the blood pool does not exist.

At block 615, basal and apical layer identification is performed. Basal and apical slices are determined by detecting the orientation of the long axis of the LV based on the endocardium size in image slices either side of the mid-cavity layer. The image slices on both sides of the mid-cavity are grouped separately and the average endocardium size is calculated for each group. The larger average size group is identified as the basal layer, whereas the smaller average size group is identified as the apical layer.

At block 603, short-axis partitioning is performed. Following block 602, slices are labeled with a layer and the slices within the layer are sequential. Each slice is partitioned into regions to identify a circumferential location. Short-axis partitioning includes septum extraction 616, correction of segments for apical slices 617 and labeling of segments 618.

In the AHA 17 segment model the basal and mid-cavity slices are divided into 6 segments of approximately 60 degrees taking into consideration all of the septum landmarks, whereas the apical slices have 4 segments and the 17th segment is the apex. The AHA 17 segment model specifies that the upper and lower junction between the right ventricular wall and the inter-ventricular septum of the basal (and mid-cavity) slices at the end-diastolic phase can be used to identify different segments. For each image, there are four sub-steps to locate the anterior and inferior ends of the inter-ventricular septum. FIG. 7 through FIG. 10 illustrate the process.

Figure 7:
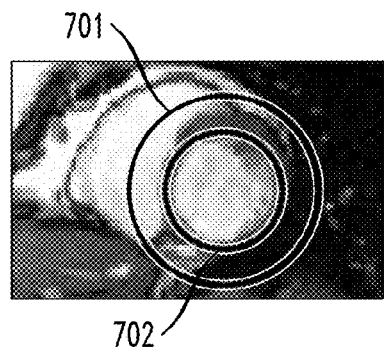
FIGS. 7-10 illustrate of a method of generating a boundary of each segment according to an exemplary embodiment of the present invention.

FIG. 7 shows the generation of a cylinder 701-702 for each slice in basal, mid-cavity and apical layers. The center of the inner circle 701 is the centroid of the endocardium (LV inner wall). The inner circle radius $r_1$ is the mean radial length of the LV inner boundary from its centroid. The outer circle 702 radius $r_2=r_1+e$ millimeters (mm), where e is a parameter to the system that ensures that the region of interest (ROI) completely encapsulates the myocardium even if it is abnormally thick. A clinically normal LV thickness is 12 mm or less, and therefore e should be greater than 12. The cylinder ROI includes three types of pixels representing the right ventricle (RV) blood pool, the myocardium and the lung.

Figure 8:

FIG. 8 shows a polar transformation applied to the ROI to form a rectangular image 801. Transforming the image into a polar coordinate system eases calculation and visualization. In one or more embodiments, the RV area is split into two parts after transformation. Therefore, the rectangular image is duplicated and joined by the same image to avoid this issue. The RV blood pool and myocardium occupy the major part of the ROI region; hence, the intensity distribution can be classified. The ROI is binarized using Otsu thresholding (802). The largest region is then selected as the RV blood pool (803). Its edges are identified to locate the two ends of the septum.

Figure 9:
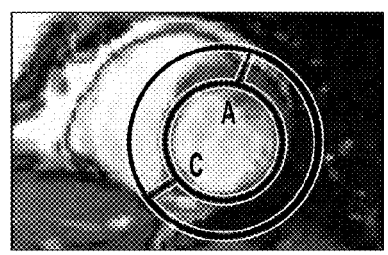
Figure 10:
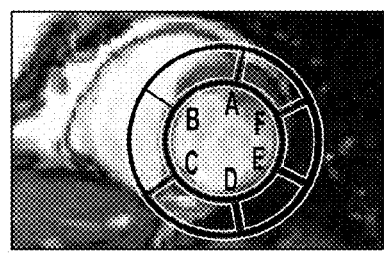

FIG. 9 shows the septal region mapped back to the original image. Two lines are generated, A and C, representing the anterior and inferior ends of the inter-ventricular septum respectively as determined by the edges identified in 803.

At block 617, the septal extraction operates under the assumption that the RV blood pool is the largest bright region in the cylinder ROI. In some of the slices of the apical layer, the blood pool becomes small or does not exist at all as the slice is below the right ventricle and there is no actual blood pool. This can lead to variation among the resulting segments of apical slices with the initial septal extraction. To deal with this problem, additional measures are used. The slices in the mid-cavity layer have a relatively bigger right ventricle blood pool compared to other slices. The septum extracted from those slices is considered to be more reliable than from other slices. A check is performed as to whether the septum extracted in the basal and apical layers is consistent with the mid-cavity layer by measuring the shift in detected septal regions between adjacent slices. If the shift is above a threshold, the septal boundary found in the previous slice is used as a reference point to the one in the current slice.

Starting with the first slice in the apical layer adjacent to the mid-cavity, the distance of each of the extracted lines ($A_{curr}$ and $C_{curr}$) in the current slice from their respective location in the previous slice ($A_{pre}$ and $C_{pre}$) is determined. The assumption is that the distance should be small enough such that the septums extracted in the two slices are consistent. If the distance is bigger than the slice thickness, it suggests that the septum is not extracted properly in that slice. The lines $A_{curr}$ and $C_{curr}$ need to be recalculated. Let $A_{inner,curr}$; $A_{outer,curr}$ be the start and end point of the line A, respectively. In order to find the updated line A, $A_{inner,curr}$ is set to be point on the LV inner boundary that is closest to $A_{inner,pre}$ in the previous slice. $A_{outer,curr}$ is the point on the LV outer boundary that is closest to $A_{outer,pre}$. The same process is applied to update $C_{curr}$ using $C_{pre}$ on the previous slice and the entire routine is repeated for each slice in the apical layer.

At block 618, segment labeling is performed. Given the upper and lower LV/RV junction points determined in the aforementioned steps, segments 2 and 3 (FIG. 2) and 8 and 9 (FIG. 3) are found by dividing evenly the region between the two junction points along the circumference of the ROI (line B in FIG. 10), and the other four segments (1, 4, 5, 6 in FIGS. 2 and 7, 10, 11, 12 in FIG. 3) are extracted by finding the opposite lines (180° along the circumference of the ROI) corresponding to the first three segment lines in the septal region (lines D, E and F in FIG. 10). For segments 13, 15 and 16 (FIG. 4), only the opposite lines of A and C (FIG. 9) are determined. To detect the orientation of the LV and allow segment labeling, the lung is segmented in one of the basal or mid-cavity slices. Lung tissue has a relatively low signal in MR images and appears as dark areas. In the chosen slice, a new circular ROI is extracted with the center as the centroid of the endocardium boundary and with a radius of f mm, where f is a parameter to the system that is large enough to include a significant portion of lung tissue in the ROI. It should be understood that f can be selected by one of ordinary skill in the art and that the "significant portion of the lung" would be understood, for example, to balance the inclusion of portions of the lung tissue in the ROI while excluding other tissue(s). The ROI is thresholded to obtain a binary mask where the biggest component is extracted and identified as the lung. The distance between the centroid of the two lines (A and C) and the centroid of the lung are computed. The line with the shorter distance to the lung is labeled as the division between the anteroseptal and anterior region while the other as the line that separates the inferoseptal and inferior regions. Thus, the circumferential locations in the basal and mid-cavity are determined. The circumferential locations are: anterior, anteroseptal, inferoseptal, inferior, inferolateral, and anterolateral; for apical, the four segments are: anterior, septal, inferior, and lateral. Table 1 shows the assignment strategy:

TABLE 1

The assignment of regions by using information from layer ID and extracted lines. The assumption is: A is the line that represents the end of the inter-ventricular septum closest to the lung.

| ID | layer | sub-region | Lines |
|---|---|---|---|
| 1 | basal | anterior | F->A |
| 2 | basal | anteroseptal | A->B |
| 3 | basal | inferoseptal | B->C |
| 4 | basal | inferior | C->D |
| 5 | basal | inferolateral | D->E |
| 6 | basal | anterolateral | E->F |
| 7 | mid-cavity | anterior | F->A |
| 8 | mid-cavity | anteroseptal | A->B |
| 9 | mid-cavity | inferoseptal | B->C |
| 10 | mid-cavity | inferior | C->D |
| 11 | mid-cavity | inferolateral | D->E |
| 12 | mid-cavity | anterolateral | E->F |
| 13 | apical | anterior | F->A |
| 14 | apical | septal | A->C |
| 15 | apical | inferior | C->D |
| 16 | apical | lateral | D->F |
| 17 | apex | — | — |

At block 607, the output 1 includes a 3D segment mask. All tissue in LV is assigned to an anatomical segment label.

At block 608, a measurement function is applied to the 3D segment mask 607 to determine the value of the regional functional parameter to display in the polar map 611. Optional additional inputs 609 to this function may include other 3D segment masks generated by the method in FIG. 6 (blocks 601 to 603) but using as input a volumetric MR image series 605, and associated wall boundaries 606 from a different time point in the heart cycle. Other optional inputs 609 could be any related data required to calculate the specific measurement function. Operating upon multiple inputs in the measurement function allows the display in the polar map 611 of relative regional functional parameters such as LV wall (myocardium) motion.

At block 610, a regional linear mapping (image→polar map) is performed. In the polar map, the anatomical locations are superimposed and are consistent with the AHA 17 segment standard. In the previous steps, the segments have been automatically extracted from all slices at a certain time phase. In order to plot the feature extracted from a slice to the polar map, the radius and angle for each voxel is determined. A standard polar map 100, with 17 segments (shown in FIG. 1) is generated. The radius R of each layer l is determined: Let apex layer $R_1=0.5$ unit, apical layer $R_2=1.5$ unit, mid-cavity layer $R_3=2.5$ unit and basal layer $R_4=3.5$ unit. Let $n_l$ be the total number of slices in layer l, the radius $r_{s,l}$ at s-th slice in layer l is defined as, $$r_{s,l} = \frac{s(R_l - R_{l-1})}{n_l} + R_{l-1}$$

where $R_0=0$, for all l in the range of [1 2 3 4].

Figure 11:
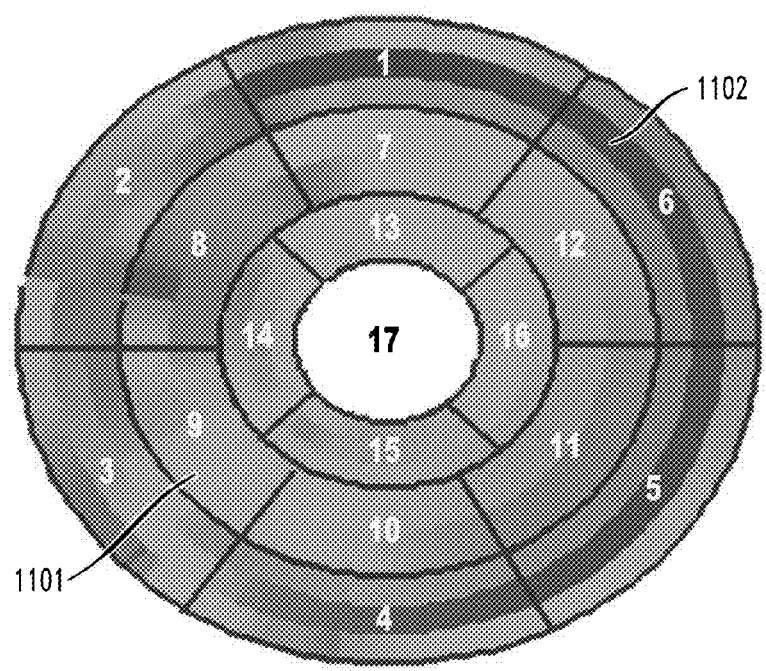
FIG. 11 is a polar map according to an exemplary embodiment of the present invention.

After the radius of a slice has been determined, the information determined for each anatomical region is linearly mapped to the corresponding regions in the segment polar map. The same strategy is then applied to all slices. A segment polar map with parameter map is then generated as shown in FIG. 11, where here the color gradient (illustrated in grey-scale) relates to the thickness of the myocardium (heart wall) as an example. In FIG. 11 darker areas (e.g., 1102) reflect thicker myocardium and mid-range and lighter areas (e.g., 1101) reflect normal myocardium.

At block 612, the regional linear mapping (e.g., from the polar map to the image) is performed. This process associates all pixels in the polar map to the corresponding tissue in the MR images that are used to generate the polar map. The 2-way link of the polar map and the MR images allows the user to click on any pixel in the polar map to find the corresponding location in a specific MR image, and vice versa.

Let P be a point in the polar map, the goal is to compute the location k on the s-th slice in the MR image series. In the flowchart in FIG. 6, in block 602 it is known to which layer each image slice belongs. From the polar map, let l be the layer ID and r the radius of the chosen point. Based on the above information the slice ID, s can be determined as, $s=\text{floor}((r-R_{l-1})*n_l/(R_l-R_{l-1}))$ where $R_l$ is the radius of the layer l, and $n_l$ is the number of slices in that layer that is obtained from block 602 in FIG. 6.

After the slice ID of the point P is determined, the location k on that slice needs to be generated. In the process shown in FIGS. 7-10, the boundaries of each segment (Lines A, B, C, D, E, F) are obtained. By linearly mapping the point P in its selected segment to the corresponding segment in the LV, the location on the s-th slice can be found.

At block 611, the output includes a 2-D polar map to present regional functional parameters of the LV. The 2-D polar map offers features including:

1. The functional measurements or parameters for all LV tissue are presented in the polar map with the label of the anatomical regions. The polar map allows a user to visualize the overall distribution of the functional parameters, especially identify suspicious regions with abnormal parameters.

2. The polar map is able to visualize the granular details for all tissue in the LV.

3. The polar map has a 2-way 1-to-1 mapping to the corresponding location in the MR image. It allows the users to find the regions in the MR image that shows abnormal parameters in the polar map. In this way, the users not only are able to see the overall distribution of the parameters with the segment labeled, but they can also directly go to the corresponding location in the MR image (e.g., by clicking on the problematic regions on the polar map).

It should be understood that the methodologies of embodiments of the invention may be particularly well-suited for automatic segment extraction and visualization. Furthermore, the disclosure is not limited to MRI and embodiments are application to other imaging systems, such as computed tomography (CT), positron emission tomography-computed tomography (PET-CT), and the like.

By way of recapitulation, according to an exemplary embodiment of the present invention, a method for automatically generating a polar map of the LV in a segment model (see FIG. 6) includes long-axis partitioning 602, short-axis partitioning 603, and polar map generation 604. The method is applied on all 2D MR slices of a certain time phase in a cine cardiac MRI, such as end-diastole. The method takes input 601 including a volumetric MR image series 605 with the associated myocardial boundaries 606. The method outputs a parametric segment mask 607 for all tissue in the LV, a polar map 611 to represent the regional functional parameters extracted from the LV 610, and a mapping from the polar map to the anatomical location in the cardiac MRI series 612.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a system for feedback collection and analysis. Further, a computer program product can include a tangible computer-readable recordable storage medium with code adapted to be executed to carry out one or more method steps described herein, including the provision of the system with the distinct software modules.

Figure 12:
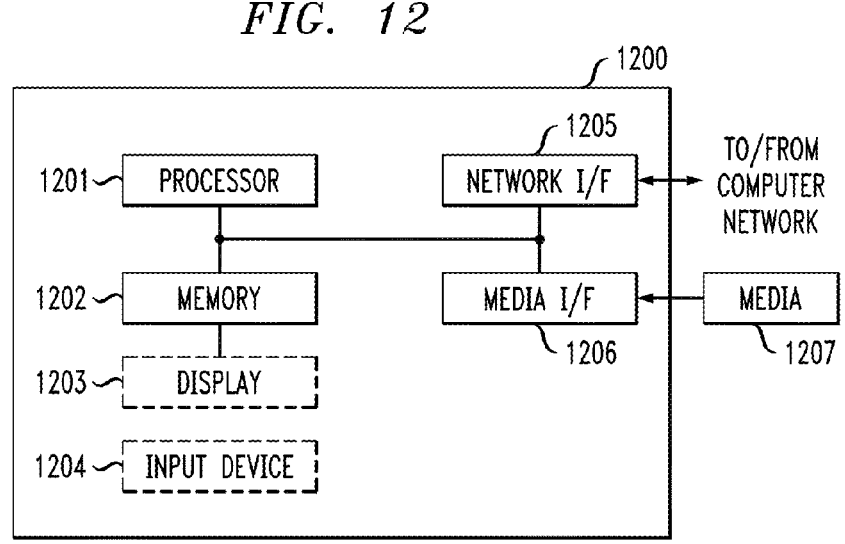
FIG. 12 is a diagram of a computer system configured for feedback collection and analysis according to an exemplary embodiment of the present invention.

Referring to FIG. 12; FIG. 12 is a block diagram depicting an exemplary computer system 1200 for automatic segment extraction according to an embodiment of the present invention. The computer system shown in FIG. 12 includes a processor 1201, memory 1202, display 1203, input device 1204 (e.g., keyboard), a network interface (I/F) 1205, a media IF 1206, and media 1207, such as a signal source, e.g., camera, Hard Drive (HD), external memory device, etc.

In different applications, some of the components shown in FIG. 12 can be omitted. The whole system shown in FIG. 12 is controlled by computer readable instructions, which are generally stored in the media 1207. The software can be downloaded from a network (not shown in the figures), stored in the media 1207. Alternatively, software downloaded from a network can be loaded into the memory 1202 and executed by the processor 1201 so as to complete the function determined by the software.

The processor 1201 may be configured to perform one or more methodologies described in the present disclosure, illustrative embodiments of which are shown in the above figures and described herein. Embodiments of the present invention can be implemented as a routine that is stored in memory 1202 and executed by the processor 1201 to process the signal from the media 1207. As such, the computer system is a general-purpose computer system that becomes a specific purpose computer system when executing routines of the present disclosure.

Although the computer system described in FIG. 12 can support methods according to the present disclosure, this system is only one example of a computer system. Those skilled of the art should understand that other computer system designs can be used to implement embodiments of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although illustrative embodiments of the present invention have been described herein with reference to the accompanying drawings, it is to be understood that the invention is not limited to those precise embodiments, and that various other changes and modifications may be made therein by one skilled in the art without departing from the scope of the appended claims.

What is claimed is:

1. A computer program product for automatically identifying and localizing anatomical regions of a left ventricle of a heart using a segment model, the computer program product comprising a computer readable storage medium having program instructions embodied therewith, the program instructions executable by a processor to cause the processor to perform a method comprising:

receiving a volumetric image series of a certain phase in a heart cycle with associated myocardial boundaries, representing the heart;

performing a long-axis partitioning on each image of the volumetric image series;

performing a short-axis partitioning on each image of the volumetric image series;

generating a parametric segment mask defining a plurality of segments of volumetric images of the volumetric images series and assigning anatomical segment labels to the plurality of segments of the volumetric images of the volumetric image series, wherein generating the parametric segment mask further comprises determining, in the short-axis partitioning on each image of the volumetric image series, an inner radius of a cylinder for each slice of the volumetric image series, and determining an outer radius of the cylinder by adding a predetermined thickness to the inner radius;

applying a measurement function to the parametric segment mask to determine a plurality of regional functional parameters of a plurality of segments of the volumetric images, wherein the plurality of segments correspond to the anatomical segment labels;

generating a polar map comprising a plurality of segments consistent with a segment standard for myocardial boundaries by mapping the plurality of regional functional parameters determined for each of the plurality of segments of the volumetric images to the plurality of segments consistent with the segment standard for myocardial boundaries, wherein the polar map is a visual representation of the plurality of regional functional parameters of the plurality of segments of the volumetric images for the certain phase determined by applying the measurement function to the parametric segment mask and mapped to the plurality of segments of the polar map; and generating a mapping from each of a plurality of points in the polar map to a corresponding voxels in the volumetric image series representing one or more anatomical locations in the volumetric image series, wherein each of the anatomical locations is characterized using the long-axis partitioning and the short-axis partitioning, and wherein the mapping facilitates selectable links between the plurality of points in the polar map and the corresponding voxels in the volumetric image series.

2. The computer program product of claim 1, further comprising automatically generating the polar map.

3. The computer program product of claim 1, wherein the plurality of regional functional parameters are represented in the polar map by a color range and the anatomical location is directly related to a specific segment of the polar map.

4. The computer program product of claim 1, wherein the polar map displays the plurality of regional functional parameters for a plurality of layers of the heart captured by the volumetric image series at the certain phase of the heart.

5. The computer program product of claim 1, the polar map has a 1-to-1 linkage from the points in the polar map to the voxels in the volumetric image series.

6. The computer program product of claim 5, further comprising receiving an indication of one of the points in the polar map and outputting a corresponding tissue or its regional functional parameters.

7. The computer program product of claim 1, wherein the mapping is a regional linear mapping facilitating identification of a location in the anatomical location via user selection of a pixel of the polar map, wherein the pixel is one of the points.

8. The computer program product of claim 1, wherein the mapping is a regional linear mapping facilitating identification of a pixel of the polar map via user selection of a location in the anatomical location, wherein the pixel is one of the points.

9. The computer program product of claim 1, wherein applying the measurement function to the parametric segment mask determines a plurality of regional functional parameters within each of the plurality of segments of the volumetric image.

* * * * *